United States Patent
Dykhuizen et al.

(10) Patent No.: US 12,202,808 B2
(45) Date of Patent: *Jan. 21, 2025

(54) SUBSTITUTED ANTIVIRALS FOR TREATING CORONAVIRUS INFECTION

(71) Applicants: Erasmus University Medical Center Rotterdam, Rotterdam (NL); Purdue Research Foundation, West Lafayette, IN (US)

(72) Inventors: Emily Carla Dykhuizen, West Lafayette, IN (US); Mart Matthias Lamers, Rotterdam (NL); Bartholomeus Leonardus Haagmans, Abcoude (NL); Tokameh Mahmoudi, Rotterdam (NL)

(73) Assignees: Erasmus University Medical Center Rotterdam, Rotterdam (NL); Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/068,744

(22) Filed: Dec. 20, 2022

(65) Prior Publication Data

US 2023/0192634 A1 Jun. 22, 2023

Related U.S. Application Data

(60) Provisional application No. 63/292,032, filed on Dec. 21, 2021.

(51) Int. Cl.
| | | |
|---|---|---|
| *C07D 273/02* | (2006.01) | |
| *A61K 9/00* | (2006.01) | |
| *C07D 273/08* | (2006.01) | |
| *C07D 413/10* | (2006.01) | |

(52) U.S. Cl.
CPC .......... *C07D 273/08* (2013.01); *A61K 9/0019* (2013.01); *A61K 9/0043* (2013.01); *C07D 413/10* (2013.01)

(58) Field of Classification Search
CPC ..... C07D 273/08; C07D 273/02; A61P 31/12; A61K 31/395
USPC ....................................... 540/469
See application file for complete search history.

(56) References Cited

U.S. PATENT DOCUMENTS

| 11,267,809 B2 * | 3/2022 | Chory et al. | ......... C07D 413/14 |
| 2020/0255416 A1 * | 8/2020 | Chory et al. | ......... C07D 413/14 |

FOREIGN PATENT DOCUMENTS

| WO | 2009026527 A1 | 2/2009 | |
| WO | WO 2020/014524 A1 * | 1/2020 | ........... A61K 31/395 |
| WO | 2021191312 A1 | 9/2021 | |

OTHER PUBLICATIONS

Wei et al., (Cell 184, 76-91, 2021, Genome-wide CRISPR Screens Reveal Host Factors Critical for SARS-CoV-2 Infection (Year: 2021).*
Marian et al., 2018, (Cell Chemical Biology 25, 1443-1455, Dec. 20, 2018, Small Molecule Targeting of Specific BAF (mSWI/SNF) Complexes for HIV Latency Reversal) (Year: 2018).*
Milad Shirvaliloo, (Epigenomics 13(10), 745-750, Apr. 2021 Epigenomics in COVID-19; the link between DNA methylation, histone modifications and SARS-CoV-2 infection) (Year: 2021).*
Jul. 19, 2022 (EP) Extended European Search Report Application No. 22153463.9.
Shirvaliloo, Milad. "Epigenomics in COVID-19; the link between DNA methylation, histone modifications and SARS-CoV-2 infection" Epigenomics 2021, 13(10) 745-750.
Marian et al. "Small Molecule Targeting of Specific BAF (mSWI/SNF) complexes for HIV Latency Reversal" Cell Chemical Biology, Elsevier, vol. 25, No. 12, 2018, 1443-1455.
Wei et al. "Genome-wide CRISPR Screens Reveal Host Factors Critical for SARS-CoV-2 Infection" 2021, Cell 184, 76-91.

* cited by examiner

*Primary Examiner* — Douglas M Willis
(74) *Attorney, Agent, or Firm* — Banner & Witcoff, Ltd.

(57) ABSTRACT

The invention provides a BAF complex modulating compound for use as a coronavirus antiviral; wherein the BAF complex modulating compound is of Formula (I):

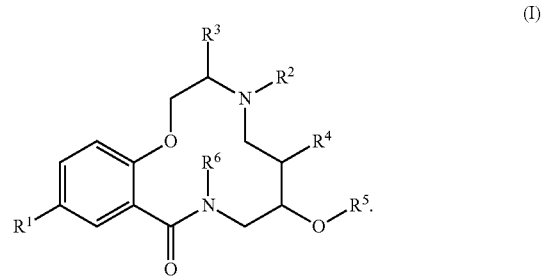

(I)

17 Claims, 1 Drawing Sheet

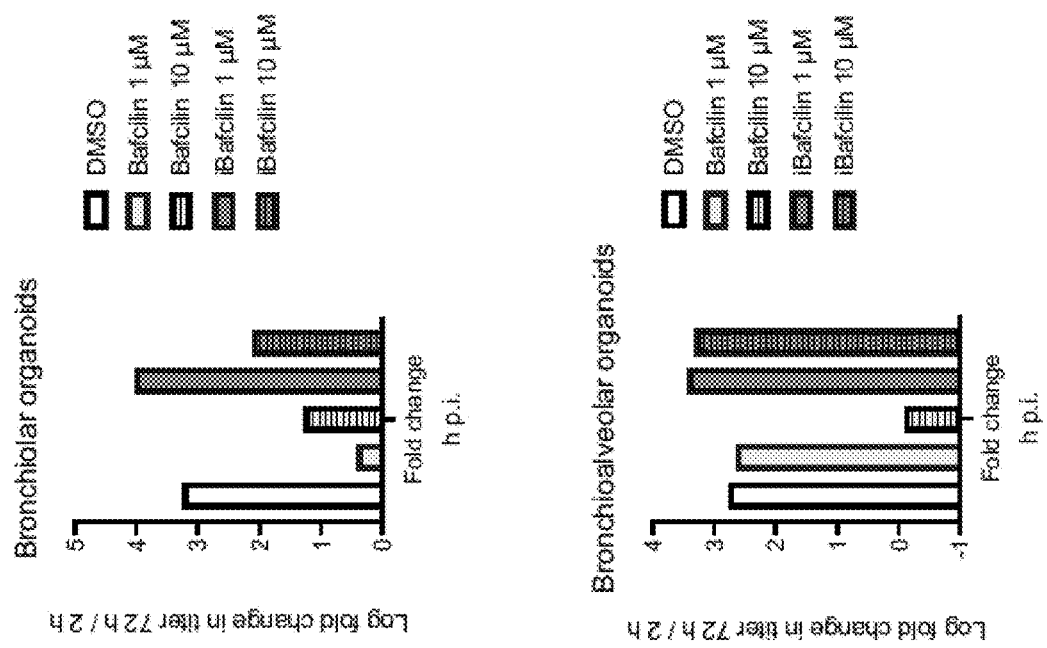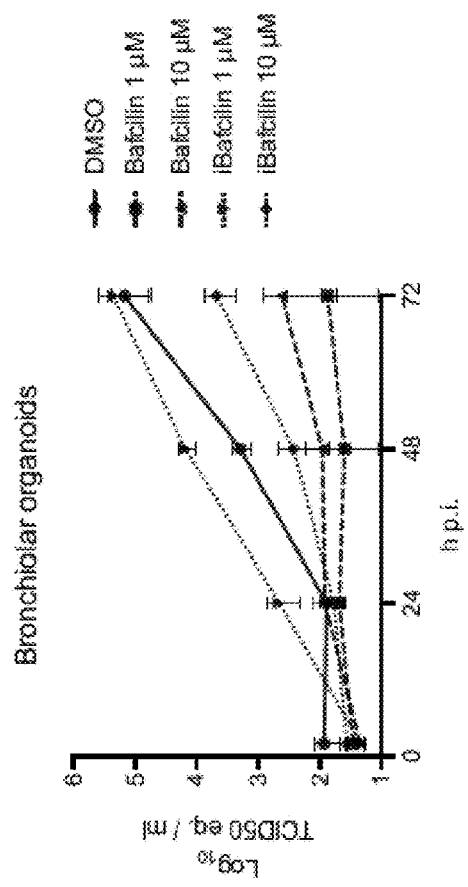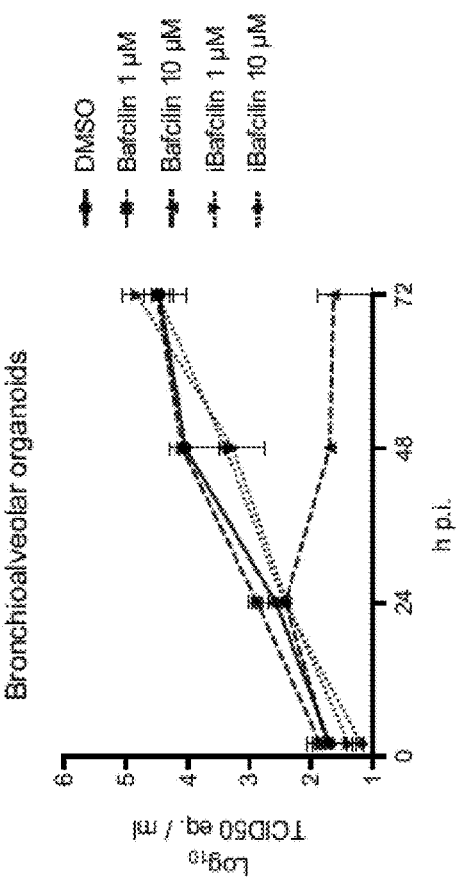

SUBSTITUTED ANTIVIRALS FOR TREATING CORONAVIRUS INFECTION

RELATED APPLICATIONS

This application claims the benefit of U.S. Provisional Application No. 63/292,032 and filed Dec. 21, 2021 which is hereby incorporated by reference in its entirety.

FIELD OF THE INVENTION

The invention is in the field of medicine, more specifically antiviral therapy for treating or preventing coronavirus infection such as SARS-CoV-2 infection. The invention provides medical uses for coronavirus antiviral compounds or agents. More specifically, the invention relates to BAF complex modulating compounds, preferably BAF complex modulating compounds that inhibit ARID1A subunit-containing BAF complexes, for use in treating or preventing coronavirus infection in a subject.

BACKGROUND OF THE INVENTION

Antiviral therapies are being investigated alongside vaccines for the treatment and prevention of COVID-19. These investigational antiviral therapies are generally designed to target and inhibit different phases of the virus life cycle, such as viral entry (via the angiotensin-converting enzyme 2 (ACE2) receptor and transmembrane serine protease 2 (TM-PRSS2)), viral membrane fusion and endocytosis, or the activity of the SARS-CoV-2 3-chymotrypsin-like protease (3CLpro) and the SARS-CoV-2 RNA-dependent RNA polymerase.

At this moment, according to the Antiviral Therapy section of the COVID-19 Treatment Guidelines of the National Institute of Health (NIH), remdesivir is the only FDA-approved antiviral drug for the treatment of COVID-19. More specifically, remdesivir is approved by the FDA for the treatment of COVID-19 in hospitalized adult and pediatric patients.

Currently, the NIH COVID-19 Treatment Guidelines Panel does not recommend the use of other antivirals such as ivermectin, and advises against the use of nitazoxanide, hydroxychloroquine, chloroquine and azithromycin. The panel also advises against the use of HIV protease inhibitors such as lopinavir and ritonavir.

Wei et al. (Cell, 184, 76-91 (2021)) describes basic research in which a genome-wide CRISPR screen in Vero-E6 cells was performed that revealed certain host factors associated with SARS-CoV-2 infection. Some SARS-CoV-2 resistance genes revealed by the CRISPR knockout screen were related to the SWI/SNF chromatin remodeling complex. Wei et al. do not disclose any experimentation with small molecules that inhibit ARID1A-containing SWI/SNF chromatin remodeling complexes, the latter also being referred to as the BAF complex in mammalian cells.

There is a need for SARS-CoV-2 antiviral agents that can be used to treat or prevent coronavirus infection.

SUMMARY OF THE INVENTION

The inventors unexpectedly discovered that a previously identified compound class of BAF complex modulating compounds, which specifically inhibit ARID1A-containing BAF complexes, can be used as an antiviral in the treatment or prevention of a coronavirus infection. This compound class has inter alia been described by Marian et al. (Cell Chemical Biology 25, 1443-1455 (2018)) and in WO 2020/014524 A1 in relation to HIV latency reversal. This compound class has also been described in US 2020/0255416 A1 in relation to cancer combination therapy.

Therefore, the invention provides a BAF complex modulating compound for use as a coronavirus antiviral (in a subject); wherein the BAF complex modulating compound is of Formula (I):

(I)

[Chemical structure of Formula (I)]

wherein $R^1$ is selected from the group consisting of amine, substituted amine, alkylaminocarbonylamino, substituted alkylaminocarbonylamino, alkanoylamino, substituted alkanoylamino, arylaminocarbonylamino, substituted arylaminocarbonylamino, carbamate, substituted carbamate, aroylamino and substituted aroylamino;

wherein $R^2$ is selected from the group consisting of heteroaryl-aryl-alkyl, substituted heteroaryl-aryl-alkyl, aryl-heteroaryl-alkyl, substituted aryl-heteroaryl alkyl, alkanoyl and substituted alkanoyl;

wherein $R^3$ to $R^6$ are each independently selected from the group consisting of H, alkyl and substituted alkyl;

or a pharmaceutically acceptable salt, polymorph, hydrate, solvate, prodrug or active metabolite thereof.

In embodiments, if an absolute stereochemistry is not expressly indicated, then each center may independently be of R-configuration or S-configuration or a mixture thereof. In certain embodiments of formula (I), the stereochemistry at C2, C5 and C6 is configured to provide the S, S, R stereoisomer at C2, C5 and C6 respectively. In other embodiments, the stereochemistry of the compound of formula (I) is configured to provide the R, S, R stereoisomer at C2, C5 and C6 respectively.

In a preferred embodiment of a compound for use according to the invention, the BAF complex modulating compound is of formula (IA):

(IA)

[Chemical structure of Formula (IA)]

wherein $R^1$ is selected from the group consisting of amine, substituted amine, alkylaminocarbonylamino, substituted alkylaminocarbonylamino, alkanoylamino, substituted alkanoylamino, arylaminocarbonylamino, substituted arylaminocarbonylamino, carbamate, substituted carbamate, aroylamino and substituted aroylamino;

wherein $R^2$ is selected from the group consisting of heteroaryl-aryl-alkyl, substituted heteroaryl-aryl-alkyl, aryl-heteroaryl-alkyl, substituted aryl-heteroaryl alkyl, alkanoyl and substituted alkanoyl;

wherein $R^3$ to $R^6$ are each independently selected from the group consisting of H, alkyl and substituted alkyl;

or a pharmaceutically acceptable salt, polymorph, hydrate, solvate, prodrug or active metabolite thereof.

In an embodiment of a compound for use according to the invention, wherein the compound is of the formula IA, the stereochemistry at C2, C5 and C6 is configured to provide the S, S, R stereoisomer at C2, C5 and C6 respectively. In another embodiment, the stereochemistry of the compound of formula (IA) is configured to provide the R, S, R stereoisomer at C2, C5 and C6, respectively.

In another embodiment of a compound for use according to the invention, the BAF complex modulating compound is of formula (IB):

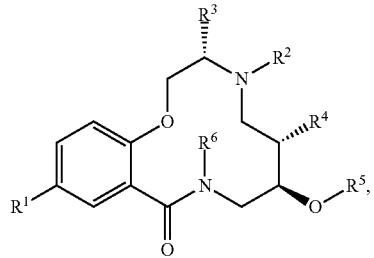

(IB)

wherein $R^1$ is selected from the group consisting of amine, substituted amine, alkylaminocarbonylamino, substituted alkylaminocarbonylamino, alkanoylamino, substituted alkanoylamino, arylaminocarbonylamino, substituted arylaminocarbonylamino, carbamate, substituted carbamate, aroylamino and substituted aroylamino;

wherein $R^2$ is selected from the group consisting of heteroaryl-aryl-alkyl, substituted heteroaryl-aryl-alkyl, aryl-heteroaryl-alkyl, substituted aryl-heteroaryl alkyl, alkanoyl and substituted alkanoyl;

wherein $R^3$ to $R^6$ are each independently selected from the group consisting of H, alkyl and substituted alkyl;
or a pharmaceutically acceptable salt, polymorph, hydrate, solvate, prodrug or active metabolite thereof.

In an embodiment of a compound for use according to the invention, wherein the compound is of the formula I, IA or IB, $R^1$ is an alkylaminocarbonylamino. Examples of alkylaminocarbonylamino groups include, but are not limited to isopropyl-NHCONH— and propyl-NHCONH.

In another embodiment of a compound for use according to the invention, wherein the compound is of the formula I, IA or IB, $R^1$ is an arylaminocarbonylamino group. A particular example of an arylaminocarbonylamino group includes, but is not limited to phenyl-NHCONH—.

In another embodiment of a compound for use according to the invention, wherein the compound is of the formula I, IA or IB, $R^1$ is an amine. Particular examples of amines include, but are not limited to —NH2 and pyrimidine-NH—.

In another embodiment of a compound for use according to the invention, wherein the compound is of the formula I, IA or IB, $R^1$ is a carbamate. A particular example of a carbamate includes, but is not limited to, isopropyl-OCONH—.

In another embodiment of a compound for use according to the invention, wherein the compound is of the formula I, IA or IB, $R^1$ is an alkanoylamino. Particular examples of alkanoylamino groups include, but are not limited to isopropyl-CONH— and propyl-CONH—.

In another embodiment of a compound for use according to the invention, wherein the compound is of the formula I, IA or IB, $R^1$ is an aroylamino. A particular example of an aroylamino group includes, but is not limited to, phenyl-CONH—.

In a preferred embodiment of a compound for use according to the invention, wherein the compound is of the formula I, IA or IB, $R^1$ is selected from the group consisting of:

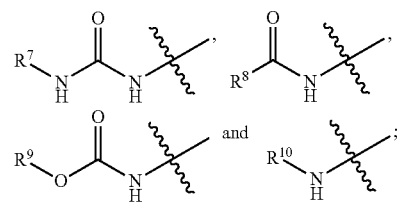

wherein $R^7$, $R^8$ and $R^9$ are each independently selected from the group consisting of alkyl, substituted alkyl, aryl, substituted aryl, heteroaryl, substituted heteroaryl, cycloalkyl, substituted cycloalkyl, heterocycle and substituted heterocycle;

wherein $R^{10}$ is selected from the group consisting of H, alkyl, substituted alkyl, aryl, substituted aryl, heteroaryl, substituted heteroaryl, cycloalkyl, substituted cycloalkyl, heterocycle and substituted heterocycle.

In an embodiment of a compound for use according to the invention, $R^7$ is alkyl or substituted alkyl. In particular embodiments, $R^7$ is methyl, ethyl, propyl, isopropyl, butyl, sec-butyl, tert-butyl, pentyl or hexyl.

In another embodiment of a compound for use according to the invention, $R^7$ is an aryl or a substituted aryl group such as phenyl or substituted phenyl.

In another embodiment of a compound for use according to the invention, $R^7$ is an heteroaryl or substituted heteroaryl.

In another embodiment of a compound for use according to the invention, $R^7$ is cycloalkyl or substituted cycloalkyl.

In another embodiment of a compound for use according to the invention, $R^7$ is a heterocycle or substituted heterocycle.

In an embodiment of a compound for use according to the invention, $R^8$ is alkyl or substituted alkyl. In particular embodiments, $R^8$ is methyl, ethyl, propyl, isopropyl, butyl, sec-butyl, tert-butyl, pentyl or hexyl.

In another embodiment of a compound for use according to the invention, $R^8$ is an aryl or a substituted aryl group such as phenyl or substituted phenyl.

In another embodiment of a compound for use according to the invention, $R^8$ is an heteroaryl or substituted heteroaryl.

In another embodiment of a compound for use according to the invention, $R^8$ is cycloalkyl or substituted cycloalkyl.

In another embodiment of a compound for use according to the invention, $R^8$ is a heterocycle or substituted heterocycle.

In an embodiment of a compound for use according to the invention, $R^9$ is alkyl or substituted alkyl. In particular embodiments, $R^9$ is methyl, ethyl, propyl, isopropyl, butyl, sec-butyl, tert-butyl, pentyl or hexyl.

In another embodiment of a compound for use according to the invention, $R^9$ is an aryl or a substituted aryl group such as phenyl or substituted phenyl.

In another embodiment of a compound for use according to the invention, $R^9$ is an heteroaryl or substituted heteroaryl.

In another embodiment of a compound for use according to the invention, $R^9$ is cycloalkyl or substituted cycloalkyl.

In another embodiment of a compound for use according to the invention, $R^9$ is a heterocycle or substituted heterocycle.

In an embodiment of a compound for use according to the invention, $R^{10}$ is H.

In another embodiment of a compound for use according to the invention, $R^{10}$ is alkyl or substituted alkyl. In particular embodiments, $R^{10}$ is methyl, ethyl, propyl, isopropyl, butyl, sec-butyl, tert-butyl, pentyl or hexyl.

In another embodiment of a compound for use according to the invention, $R^{10}$ is an aryl or a substituted aryl group such as phenyl or substituted phenyl.

In another embodiment of a compound for use according to the invention, $R^{10}$ is an heteroaryl or substituted heteroaryl.

In another embodiment of a compound for use according to the invention, $R^{10}$ is cycloalkyl or substituted cycloalkyl.

In another embodiment of a compound for use according to the invention, $R^{10}$ is a heterocycle or substituted heterocycle.

In another embodiment of a compound for use according to the invention, $R^{10}$ is a nitrogen containing heteroaryl, e.g. pyridine, pyrimidine, pyridazine, pyrazine, triazine. In embodiments, $R^{10}$ is pyrimidine.

In a preferred embodiment of a compound for use according to the invention, wherein the compound is of the formula (I), (IA) or (IB), $R^1$ is selected from the group consisting of

[chemical structures]

In preferred embodiments of a compound for use according to the invention, wherein the compound is of the formula (I), (IA) or (IB), $R^1$ is selected from the group consisting of

[chemical structures]

In a preferred embodiment of a compound for use according to the invention, wherein the compound is of the formula (I), (IA) or (IB) (with an $R^1$ group) as defined in any one of the previous aspects and/or embodiments, $R^2$ is heteroaryl-aryl-alkyl, such as 4-(pyridin-2-yl)-benzyl, 4-(pyridin-3-yl)-benzyl or 4-(pyridine-4-yl)-benzyl.

In another preferred embodiment of a compound for use according to the invention, wherein the compound is of the formula (I), (IA) or (IB) (with an $R^1$ group) as defined in any one of the previous aspects and/or embodiments, $R^2$ is aryl-heteroaryl-alkyl.

In another preferred embodiment of a compound for use according to the invention, wherein the compound is of the formula (I), (IA) or (IB) (with an $R^1$ group) as defined in any one of the previous aspects and/or embodiments, $R^2$ is alkanoyl, such as cyclopropyl-acetyl.

It will be understood that any of the $R^2$ or $R^1$ groups disclosed herein may be optionally substituted.

In a preferred embodiment of a compound for use according to the invention, wherein the compound is of the formula (I), (IA) or (IB) (with an $R^1$ group) as defined in any one of the previous aspects and/or embodiments, $R^2$ is of the formula:

$$L^1\text{-}Z \qquad \text{(IC); or}$$

$$L^2\text{-C(O)-}L^3\text{-}R^{11} \qquad \text{(ID)}$$

wherein $L^1$ is an alkyl linker or a substituted alkyl linker;
wherein $L^2$ and $L^3$ are each independently selected from the group consisting of a covalent bond, an alkyl linker and a substituted alkyl linker;
wherein Z is selected from the group consisting of heteroaryl-aryl, substituted heteroaryl-aryl, aryl-heteroaryl and substituted aryl-heteroaryl; and wherein $R^{11}$ is selected from the group consisting of alkyl, substituted alkyl, $C_{3-10}$ cycloalkyl, substituted $C_{3-10}$ cycloalkyl, $C_{3-10}$ heterocycle and substituted $C_{3-10}$ heterocycle.

In an embodiment of a compound for use according to the invention, wherein the compound is of the formula (I), (IA) or (IB) (with an $R^1$ group) as defined in any one of the previous aspects and/or embodiments, and wherein $R^2$ is of formula (IC) or (ID), $L^1$, $L^2$ or $L^3$ is a $(C_1$-$C_{12})$alkyl linker, which may be straight or branched, e.g., methyl, ethyl, n-propyl, 1-methylethyl (iso-propyl), n-butyl, n-pentyl, 1,1-dimethylethyl, (t-butyl), and the like. In some embodiments, $L^1$ is methyl. In some embodiments, $L^2$ is a covalent bond. In some embodiments, $L^3$ is methyl.

In a preferred embodiment of a compound for use according to the invention, wherein the compound is of the formula (I), (IA) or (IB) (with an $R^1$ group) as defined in any one of the previous aspects and/or embodiments, the $R^2$ group of formula (IC) is of the formula (IE):

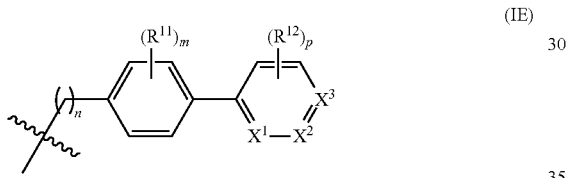

(IE)

wherein:
two of $X^1$, $X^2$ and $X^3$ are carbon atoms and one of $X^1$, $X^2$ and $X^3$ is a nitrogen atom; $R^{11}$ and $R^{12}$ are independently selected from OH, alkyl, substituted alkyl, alkenyl, substituted alkenyl, aryl, substituted aryl, alkoxy, substituted alkoxy, —OCF$_3$, —CF$_3$, halogen, azide, amine, substituted amine, amide, cycloalkyl, substituted cycloalkyl, heterocycle and substituted heterocycle;
n is an integer from 1 to 12;
m is an integer from 0 to 4; and
p is an integer from 0 to 5.

In a preferred embodiment of a compound for use according to the invention, wherein $R^2$ is of the formula (IE), $X^1$ is a nitrogen atom, $X^2$ and $X^3$ are carbon atoms, n is 1, m is 0 and p is 0. In another embodiment, $X^2$ is a nitrogen atom, $X^1$ and $X^3$ are carbon atoms, n is 1, m is 0 and p is 0. In another embodiment, $X^3$ is a nitrogen atom, $X^1$ and $X^2$ are carbon atoms, n is 1, m is 0 and p is 0.

In a preferred embodiment of a compound for use according to the invention, wherein the compound is of the formula (I), (IA) or (IB) (with an $R^1$ group) as defined in any one of the previous aspects and/or embodiments, the $R^2$ group of formula (ID) has a formula of any one of (IF1)-(IF4):

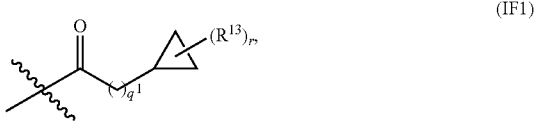

(IF1)

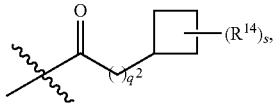

(IF2)

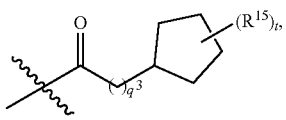

(IF3)

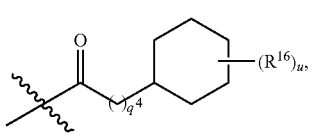

(IF4)

wherein:
$R^{13}$, $R^{14}$, $R^{15}$ and $R^{16}$ are independently selected from OH, alkyl, substituted alkyl, alkenyl, substituted alkenyl, aryl, substituted aryl, alkoxy, substituted alkoxy, —OCF$_3$, —CF$_3$, halogen, azide, amine, substituted amine, amide, cycloalkyl, substituted cycloalkyl, heterocycle and substituted heterocycle;
$q^1$ to $q^4$ are each independently an integer from 0 to 12;
r is an integer from 0 to 5;
s is an integer from 0 to 7;
t is an integer from 0 to 9; and
u is an integer from 0 to 11.

In a preferred embodiment of a compound for use according to the invention, wherein the compound is of the formula (I), (IA) or (IB) (with an $R^1$ group) as defined in any one of the previous aspects and/or embodiments, the $R^2$ group of formula (ID) is of the formula (IF1), wherein optionally $q^1$ is 1 and r is 0.

In an embodiment of a compound for use according to the invention, wherein the compound is of the formula (I), (IA) or (IB) (with an $R^1$ group) as defined in any one of the previous aspects and/or embodiments, the $R^2$ group is selected from:

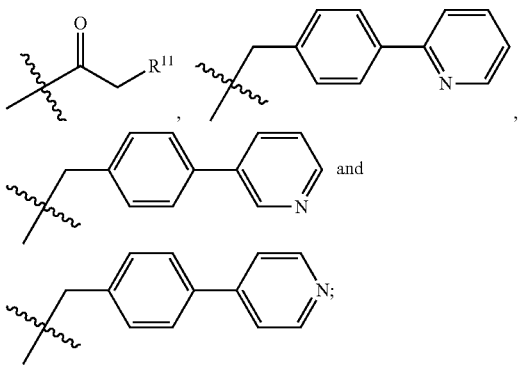

wherein $R^{11}$ is alkyl, substituted alkyl, $C_3$-$C_{10}$ cycloalkyl, substituted $C_3$-$C_{10}$ cycloalkyl, $C_3$-$C_{10}$ heterocycle or substituted $C_3$-$C_{10}$ heterocycle. In certain embodiments, $R^{11}$ is a lower alkyl, e.g., methyl, ethyl, propyl, isopropyl, butyl, sec-butyl, tert-butyl, pentyl or hexyl. In other embodiments, $R^{11}$ is selected from $C_3$-$C_{10}$ cycloalkyl, e.g, cyclopropyl, cyclobutyl, cyclopentyl, cyclohexyl, cycloheptyl, cyclooctyl. In some cases, $R^{11}$ is a cyclopropyl group.

In a preferred embodiment of a compound for use according to the invention, wherein the compound is of the formula (I), (IA) or (IB) (with an R¹ group) as defined in any one of the previous aspects and/or embodiments, the R² group is:

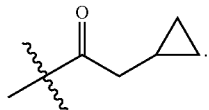 [SMILES: *C(=O)CC1CC1]

In another preferred embodiment of a compound for use according to the invention, wherein the compound is of the formula (I), (IA) or (IB) (with an R¹ group) as defined in any one of the previous aspects and/or embodiments, the R² group is:

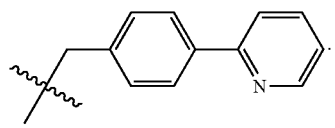 [SMILES: *Cc1ccc(-c2ccccn2)cc1]

In a preferred embodiment of a compound for use according to the invention, wherein the compound is of the formula (I), (IA) or (IB) (with an R¹ and/or R² group) as defined in any one of the previous aspects and/or embodiments, each of R³ to R⁶ is a lower alkyl group independently selected from methyl, ethyl, n-propyl, isopropyl, n-butyl, isobutyl, t-butyl, pentyl and hexyl.

In a preferred embodiment of a compound for use according to the invention, wherein the compound is of the formula (I), (IA) or (IB) (with an R¹ and/or R² group) as defined in any one of the previous aspects and/or embodiments, R³, R⁴, R⁵ and/or R6 is methyl. Preferably, each of R³, R⁴, R⁵ and R⁶ are methyl groups.

In a preferred embodiment of a compound for use according to the invention, the compound of formula (I) to (IB) is of formula (II):

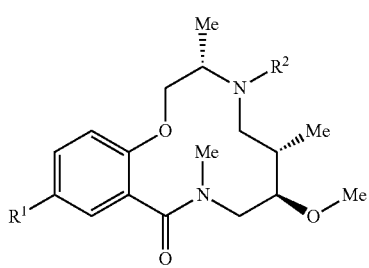

(II)

wherein:
R¹ is

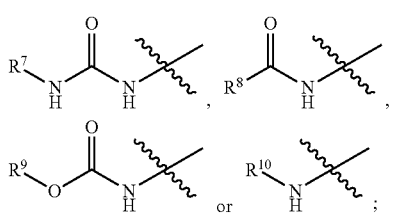

wherein R⁷, R⁸ and R⁹ are each independently selected from the group consisting of methyl, ethyl, propyl, isopropyl, butyl, sec-butyl, tert-butyl, pentyl, hexyl, aryl, substituted aryl, heteroaryl, substituted heteroaryl, cycloalkyl, substituted cycloalkyl, heterocycle and substituted heterocycle; and wherein R¹⁰ is selected from the group consisting of H, alkyl, substituted alkyl, aryl, substituted aryl, heteroaryl, substituted heteroaryl, cycloalkyl, substituted cycloalkyl, heterocycle and substituted heterocycle;
and wherein R² is selected from:

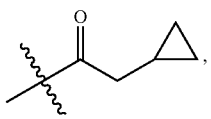

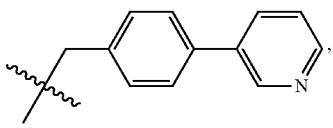

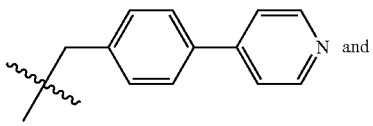

and

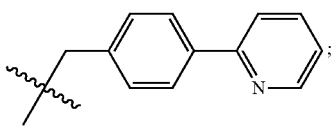

or a pharmaceutically acceptable salt, polymorph, hydrate, solvate, prodrug or active metabolite thereof.

In a preferred embodiment of a compound for use according to the invention, R² in formula (II) is

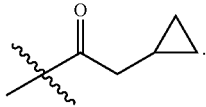 [SMILES: *C(=O)CC1CC1]

In another preferred embodiment of a compound for use according to the invention, R² in formula (II) is

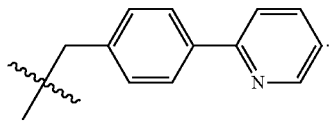 [SMILES: *Cc1ccc(-c2ccccn2)cc1]

In another preferred embodiment of a compound for use according to the invention, the compound of formula (II) is of formula (III):

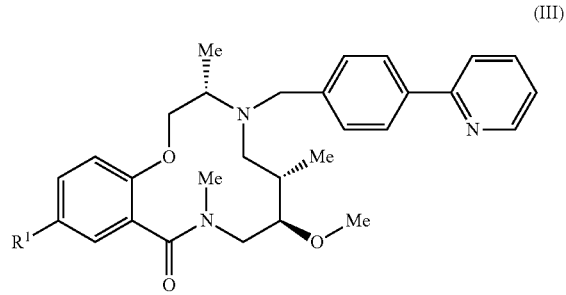

(III)

wherein:

R¹ is

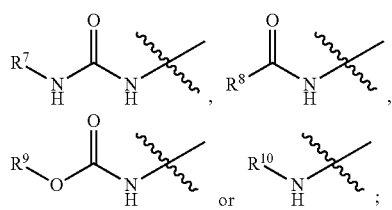

wherein

R⁷, R⁸ and R⁹ are each independently selected from the group consisting of methyl, ethyl, propyl, isopropyl, butyl, sec-butyl, tert-butyl, pentyl, hexyl, aryl, substituted aryl, heteroaryl, substituted heteroaryl, cycloalkyl, substituted cycloalkyl, heterocycle and substituted heterocycle;

and optionally wherein R¹⁰ is selected from the group consisting of H, alkyl, substituted alkyl, aryl, substituted aryl, heteroaryl, substituted heteroaryl, cycloalkyl, substituted cycloalkyl, heterocycle and substituted heterocycle;

or a pharmaceutically acceptable salt, polymorph, hydrate, solvate, prodrug or active metabolite thereof.

In another preferred embodiment of a compound for use according to the invention, the R¹ group of formulas (II) or (III) is selected from:

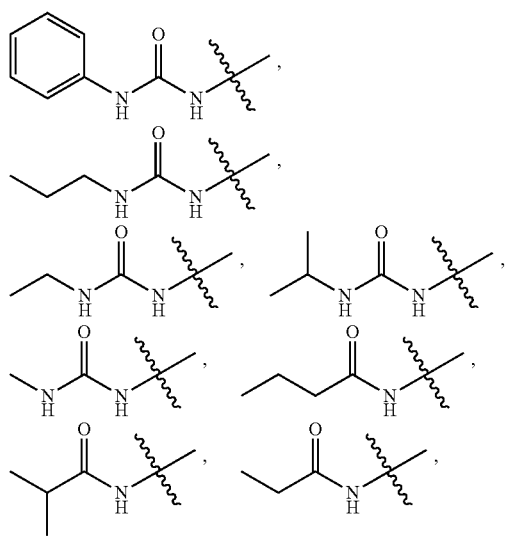

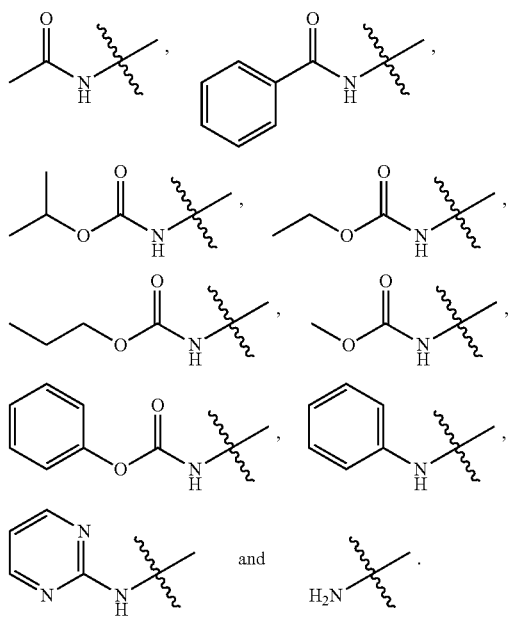

In another preferred embodiment of a compound for use according to the invention, the R¹ group of formulas (II) or (III) is selected from:

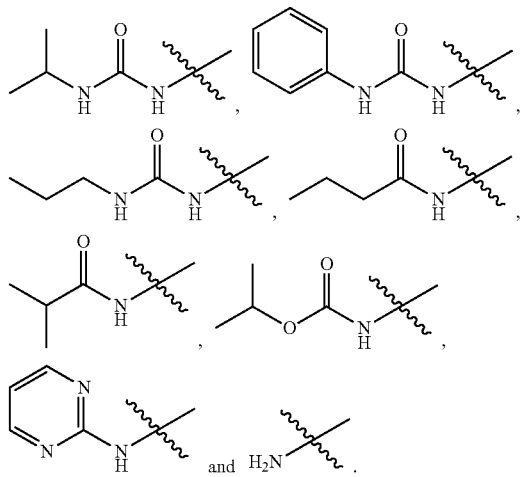

In another preferred embodiment of a compound for use according to the invention, the BAF complex modulating compound is one of the following compounds (1)-(10):

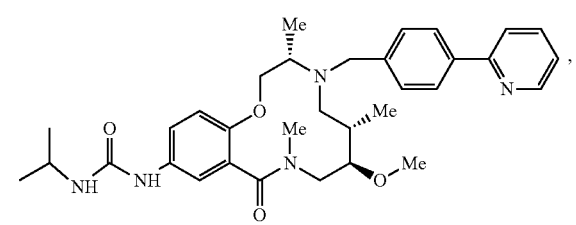

(2)
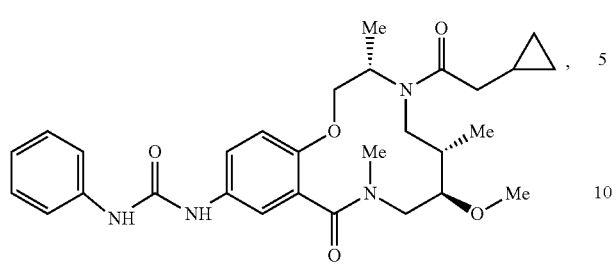
(3)
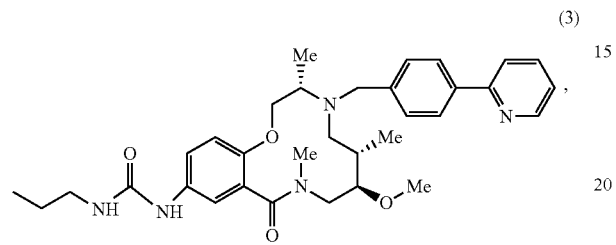
(4)
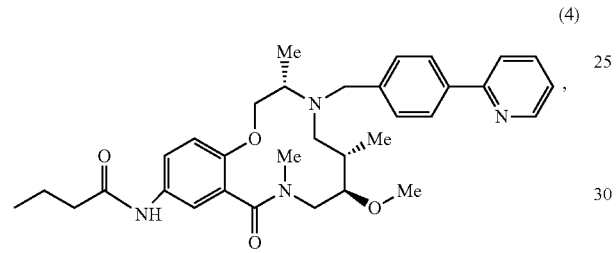
(5)
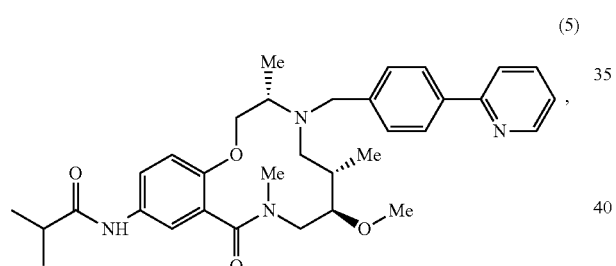
(6)
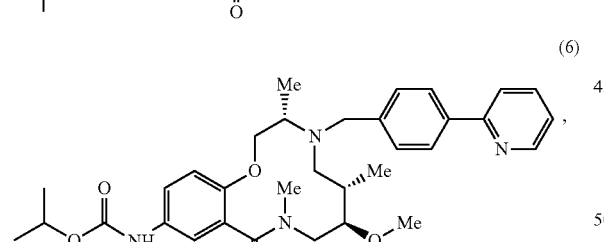
(7)
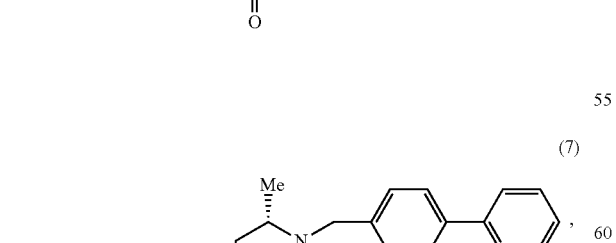
(8)
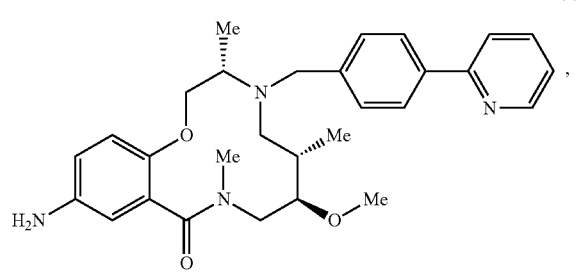
(9)
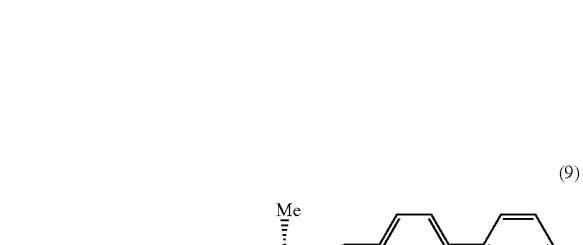
(10)
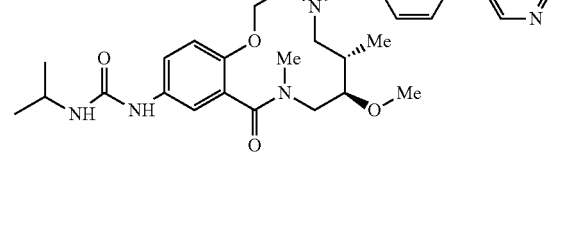
In a most preferred embodiment of a compound for use according to the invention, the BAF complex modulating compound is described by structure (1), which compound is also referred to as Baficilin1 or Bafcilin1:
(Bacfcilin1, (1))
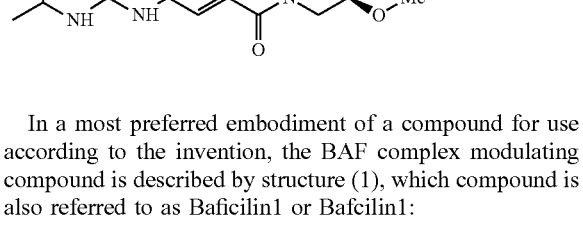
In another embodiment of a compound for use according to the invention, the BAF complex modulating compound is one of the following compounds (5) and (11)-(14):

(5)

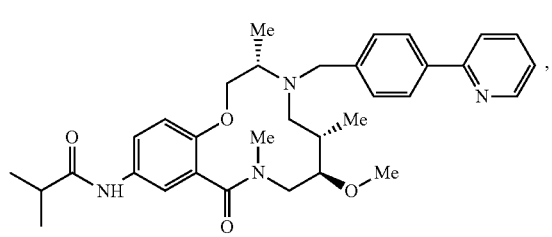

(11)

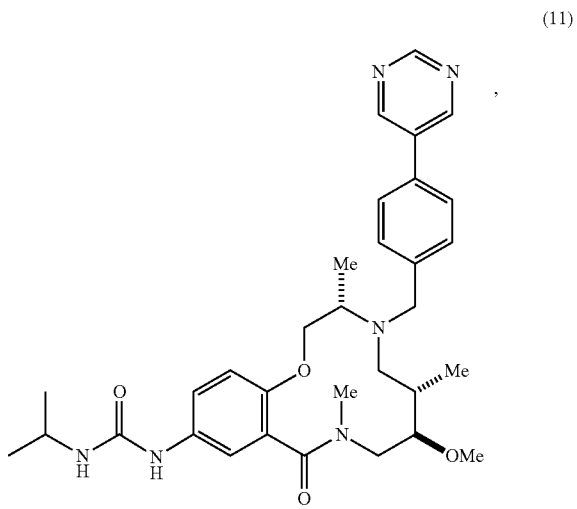

(12)

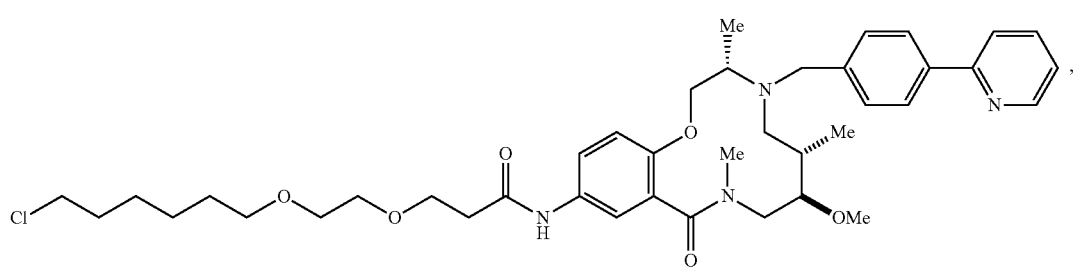

(13)

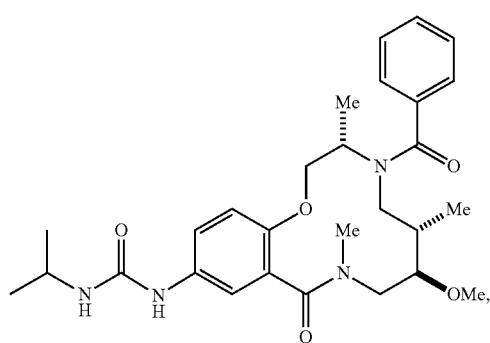

(14)

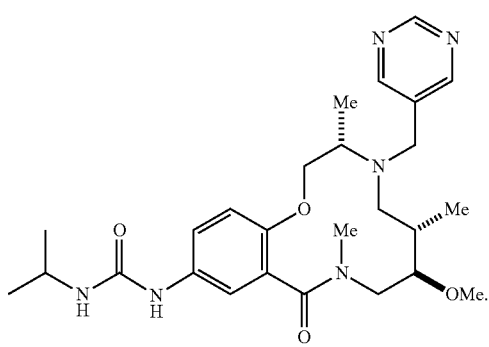

In another preferred embodiment of a compound for use according to the invention, said compound specifically inhibits a BAF complex (e.g. an ARID1A-containing BAF complex).

In another preferred embodiment of a compound for use according to the invention, said coronavirus antiviral is an oral antiviral.

In another preferred embodiment of a compound for use according to the invention, said compound is for use as a SARS-CoV-1, SARS-CoV-2 or MERS-CoV antiviral, preferably a SARS-CoV-2 antiviral.

Similarly, in another preferred embodiment of a compound for use according to the invention, said coronavirus antiviral is a COVID (such as COVID-19 or SARS) antiviral or a MERS antiviral, e.g. a COVID (such as COVID-19 or SARS) oral antiviral or a MERS oral antiviral.

In another preferred embodiment of compound for use according to the invention, said compound is for use in the treatment (which includes prevention) of a coronavirus infection in a subject.

In another preferred embodiment of a compound for use according to the invention, said subject (i) has a coronavirus infection or (ii) does not have a coronavirus infection but is at risk of coronavirus infection.

In another preferred embodiment of compound for use according to the invention, said subject is (i) at least 65 years old, (ii) immunocompromised and/or (iii) wherein the subject has at least one underlying medical condition selected from the group consisting of asthma; COPD; cystic fibrosis; pulmonary fibrosis; cardiomyopathy; pulmonary hypertension; congenital heart disease; heart failure; coronary artery disease; diabetes; obesity; cancer such as lung cancer; kidney disease; liver disease and Down syndrome.

In another preferred embodiment of a compound for use according to the invention, said subject has mild to moderate coronavirus disease, preferably mild to moderate coronavirus disease 2019 (COVID-19); and wherein said subject has at least one risk factor associated with developing severe coronavirus disease selected from (i) at least 65 years old, (ii) immunocompromised and/or (iii) at least one underlying medical condition selected from the group consisting of asthma; COPD; cystic fibrosis; pulmonary fibrosis; cardiomyopathy; pulmonary hypertension; congenital heart disease; heart failure; coronary artery disease; diabetes; obesity; cancer such as lung cancer; kidney disease; liver disease and Down syndrome.

In another preferred embodiment of a compound for use according to the invention, said coronavirus infection is a SARS-CoV infection, preferably a SARS-CoV-2 infection.

In another preferred embodiment of a compound for use according to the invention, said compound is for oral, intravenous, intranasal or (oral) inhalational administration.

In another preferred embodiment of a compound for use according to the invention, said compound is for oral administration daily or bidaily for 1-14 days, preferably wherein said compound is for administration in a unit dose of 0.1-2000 mg.

In another aspect, the invention provides a method for treating or preventing a coronavirus infection in a subject, comprising the step of:
administering a therapeutically effective amount of a BAF complex modulating compound as defined in any of the previous aspects and/or embodiments to a subject in need thereof.

In a preferred embodiment of a method for treating or preventing of the invention, said compound specifically inhibits a BAF complex (e.g. an ARID1A-containing BAF complex).

In another preferred embodiment of a method for treating or preventing of the invention, said coronavirus infection is a SARS-CoV-1, SARS-CoV-2 or MERS-CoV infection, preferably a SARS-CoV-2 infection.

In another preferred embodiment of a method for treating or preventing of the invention, said subject (i) has a coronavirus infection or (ii) does not have a coronavirus infection but is at risk of coronavirus infection.

In another preferred embodiment of a method for treating or preventing of the invention, said subject is (i) at least 65 years old, (ii) immunocompromised and/or (iii) wherein the subject has at least one underlying medical condition selected from the group consisting of asthma; COPD; cystic fibrosis; pulmonary fibrosis; cardiomyopathy; pulmonary hypertension; congenital heart disease; heart failure; coronary artery disease; diabetes; obesity; cancer such as lung cancer; kidney disease; liver disease and Down syndrome.

In another preferred embodiment of a method for treating or preventing of the invention, said compound is for oral, intravenous, intranasal or (oral) inhalational administration.

In another preferred embodiment of a method for treating or preventing of the invention, said compound is for oral administration daily or bidaily for 1-14 days, preferably wherein said compound is for administration in a unit dose of 0.1-2000 mg.

In another aspect, the invention provides a method for inhibiting or counteracting coronavirus replication, preferably SARS-CoV replication such as SARS-CoV-2 replication, in a subject, comprising the step of:—administering a therapeutically effective amount of a BAF complex modulating compound to a subject in need thereof; wherein said BAF complex modulating compound is as defined in any of the previous aspects and/or embodiments.

In another aspect, the invention provides a use of a BAF complex modulating compound as defined in any of the aspects and/or embodiments disclosed hereinabove in the manufacture of a coronavirus antiviral, preferably in the manufacture of a medicament for treating or preventing coronavirus infection in a subject. Preferably, in such a use, the coronavirus antiviral is as defined in any one of the aspects and/or embodiments disclosed herein. Preferably, in such a use, the subject is as defined in any one of the aspects and/or embodiments disclosed herein. Preferably, the coronavirus infection is as defined in any one of the aspects and/or embodiments disclosed herein.

DESCRIPTION OF THE DRAWINGS

FIG. 1. The effect of Bafcilin1 and iBafcilin on SARS-CoV-2 replication in 2D human respiratory tract organoids. (A) Replication kinetics in the presence of 1 or 10 µM Bafcilin1/'inactive' Bafcilin (iBafcilin) or DMSO (vehicle control) in bronchiolar organoids. (B) The log 10 fold change in replication between 72 and 2 hours post infection (h p.i.) from panel A. (C) Replication kinetics in the presence of 1 or 10 µM Bafcilin1/iBafcilin, or DMSO (vehicle control) in bronchioalveolar organoids. (D) The log 10 fold change in replication between 72 and 2 hours post infection (h p.i.) from panel C.

DETAILED DESCRIPTION OF THE INVENTION

Definitions

The term "BAF complex", as used herein, refers to the SWI/SNF (SWItch/Sucrose Non-Fermentable) chromatin remodeling complex in mammals such as humans. The SWI/SNF complex is a subfamily of ATP-dependent chromatin remodeling complexes, and is a group of proteins that associate to remodel the way DNA is packaged. The complex can be composed of several proteins, such as products of the SWI and SNF genes. The SWI/SNF complex generally possesses a DNA-stimulated ATPase activity that can destabilize histone-DNA interactions in reconstituted nucleosomes in an ATP-dependent manner. In embodiments, the BAF complex is the mammalian SWI/SNF-A chromatin remodeling complex (also referred to as canonical BAF; cBAF) and preferably contains ARID1A.

The term "BAF complex modulating compound", as used herein, includes reference to a class of compounds that modulate the activity of the BAF complex, preferably modulate the activity of the BAF complex by inhibiting ARID1A (subunit)-containing BAF complexes (but preferably not Polybromo-associated BAF (PBAF) complexes). Preferably, BAF complex modulating compounds as disclosed herein target a BAF-specific subunit that is ARID1A.

The term "coronavirus", as used herein, includes reference to a family of viruses also referred to as Coronaviridae or Coronavirinae, which belong to the order of Nidovirales. Preferably, the coronavirus is a virus of the subfamily of Coronaviridae, which inter alia comprises the genera of Alphacoronavirus, Betacoronavirus, Gammacoronavirus and Deltacoronavirus. Preferably, the coronavirus is a severe acute respiratory syndrome (SARS) coronavirus (SARS-CoV) such as SARS coronavirus 1 (SARS-CoV-1) or SARS-CoV-2, preferably SARS-CoV-2. Severe acute respiratory syndrome (SARS) coronaviruses are the causative agent for coronavirus disease (COVID). More specifically, SARS-CoV-2 is the causative agent for coronavirus disease 2019 (COVID-19). Testing for SARS-CoV-2 can be routinely performed, e.g. by PCR testing such as real-time reverse-transcription polymerase chain reaction (rRT-PCR) optionally combined with confirmation by nucleic acid sequencing if needed, or by LAMP (loop-mediated isothermal amplification) tests, antigen testing or serological tests, which are commonly applied throughout the world to monitor positive cases of coronavirus infection. Alternatively, the coronavirus can be a Middle East respiratory syndrome coronavirus (MERS-CoV), which is the causative agent for Middle East respiratory syndrome (MERS).

The term "COVID" or "coronavirus disease", as used herein, refers to an infectious disease caused by a severe acute respiratory syndrome coronavirus (SARS-CoV). Preferably, the SARS-CoV is SARS-CoV-2, and the COVID is COVID-2019 (also referred to as COVID-19). Common COVID symptoms include fever, cough, sore throat, malaise, headache, muscle pain, nausea, vomiting, diarrhea, and loss of taste and smell. While the majority of cases result in mild or moderate disease, some progress to severe disease characterized by e.g. pneumonia and multi-organ failure.

The term "antiviral", as used herein, includes reference to a compound, agent or drug (which terms can be used interchangeably herein) that exhibits antiviral activity, such as inhibition of viral replication, against or towards a virus pathogen. Examples of antiviral activity are amongst others interfering with the ability of a virus to enter a target cell, inhibiting uncoating of virus after cell entry, inhibiting viral replication inside a host cell, etc. Preferably, the coronavirus antiviral as disclosed herein is a SARS-CoV-1, SARS-CoV-2 or MERS-CoV antiviral, more preferably a SARS-CoV-2 antiviral. In other words, where the BAF complex modulating compounds are disclosed herein for use as a coronavirus antiviral (in a subject), the coronavirus antiviral is (i) a COVID antiviral (such as COVID-19 or SARS antiviral) or a MERS antiviral, such as a COVID oral antiviral or a MERS oral antiviral. Similarly, in embodiments, the BAF complex modulating compounds as disclosed herein are for use in coronavirus antiviral therapy, preferably COVID antiviral therapy (such as COVID-19 or SARS antiviral therapy) or MERS antiviral therapy, e.g. coronavirus oral antiviral therapy, preferably COVID oral antiviral therapy (such as COVID-19 oral antiviral therapy or SARS oral antiviral therapy) or MERS oral antiviral therapy. In embodiments, "coronavirus antiviral" can be used interchangeably with "antiviral against a coronavirus". Similarly, "coronavirus antiviral therapy" can be used interchangeably with "antiviral therapy against a coronavirus infection. Antivirals may find application in both therapeutic and prophylactic treatment of coronavirus infection. Preferably, the coronavirus antiviral as disclosed herein is an oral coronavirus antiviral such as a coronavirus antiviral in the form of a pill that is for oral administration.

The term "subject", as used herein, includes reference to a mammal, preferably a human individual, in need of a BAF complex modulating compound as disclosed herein. Preferably, the subject has a coronavirus infection or is at risk of coronavirus infection for instance because the subject has been in virus-transmissible contact with a person that has a coronavirus infection. An example of virus-transmissible contact is being part of the same household as an individual who has a coronavirus infection. Preferably, the individual is an elderly human such as a human that is at least 65, 70, 75, 80, or at least 85 years old. Alternatively, or in addition, the subject is immunocompromised and/or has at least one underlying medical condition selected from the group consisting of asthma; COPD; cystic fibrosis; pulmonary fibrosis; cardiomyopathy; pulmonary hypertension; congenital heart disease; heart failure; coronary artery disease; diabetes; obesity; cancer such as lung cancer; kidney disease; liver disease and Down syndrome. The subject can either be hospitalized or non-hospitalized. In preferred embodiments, the subject is non-hospitalized and either has a coronavirus infection or is at risk of coronavirus infection. In embodiments, the subject may not show any signs or symptoms of coronavirus disease.

The term "coronavirus infection", as used herein, includes reference to the presence of a coronavirus in a mammalian subject, preferably a human individual, optionally in combination with at least some extent of viral replication in said subject. An early stage of viral infection is viral entry and subsequent replication in a host cell. One example of a subject that has a coronavirus infection is a subject that has tested positive for a coronavirus infection by one of the standard available commercial diagnostic coronavirus tests (e.g. a PCR test), although also subjects that test negative but which in fact carry a coronavirus that has replicated at least to some extent but not sufficient in order for the test to be positive (i.e. subclinical), are considered to be subjects which have a coronavirus infection. The term "coronavirus infection" also encompasses coronavirus disease (COVID) which is an infectious disease that may either be symptomatic or asymptomatic and may result in hospitalization. The terms "virus infection" and "viral infection" can be used interchangeably. In embodiments, a coronavirus infection is one of the following four types as defined by the NIH: (1) an asymptomatic or presymptomatic infection. As an example, this type of infection may relate to subjects who test positive for SARS-CoV-2 using a virologic test (i.e., a nucleic acid amplification test (NAAT) or an antigen test) but who have no symptoms that are consistent with COVID-19. (2) Mild illness. As an example, this type of infection may relate to subjects who have any of the various signs and symptoms of COVID-19 (e.g., fever, cough, sore throat, malaise, headache, muscle pain, nausea, vomiting, diarrhea, loss of taste and smell) but who do not have shortness of breath, dyspnea, or abnormal chest imaging. In embodiments, mild illness is mild COVID. (3) Moderate illness. As an example, this type of infection may relate to subjects who show evidence of lower respiratory disease during clinical assessment or imaging and who have an oxygen saturation (SpO2)≥94% on room air at sea level. In embodiments, moderate illness is moderate COVID. (4) Severe illness. As an example, this may relate to subjects who have SpO2<94% on room air at sea level, a ratio of arterial partial pressure of oxygen to fraction of inspired oxygen (PaO2/FiO2)<300 mm Hg, a respiratory rate >30 breaths/min, and/or lung infiltrates >50%, optionally in combination with respiratory failure, septic shock, and/or multiple organ dysfunction. In embodiments, severe illness is severe COVID. Preferably, the subject to be treated does not have severe illness or severe COVID as defined above. The subject to be treated preferably has (i) an asymptomatic or presymptomatic coronavirus infection, (ii) mild illness such as mild COVID or (iii) moderate illness such as moderate COVID. In embodiments, the subject has mild to moderate COVID, preferably mild to moderate coronavirus disease 2019 (COVID-19).

Preferably, in a BAF complex modulating compound for use according to the invention, the subject has tested positive for a coronavirus (infection), such as SARS-CoV-2 (infection). In other words, the subject to be treated is a subject with a positive coronavirus, such as SARS-CoV-2, diagnostic test (result).

In embodiments, the subject has (i) a laboratory confirmed SARS-CoV-2 infection with sample collection ≤7 (such as ≤5) days prior to therapy start and/or (ii) had initial onset of one or more signs or symptoms attributable to COVID-19 for ≤7 (such as ≤5) days prior to therapy start and at least one sign or symptom attributable to COVID-19 on the day of therapy start.

In preferred embodiments of a BAF complex modulating compound for use according to the invention, the BAF complex modulating compound is for administration within 5 days or within 7 days after symptom onset or within 5 days or within 7 days after testing positive for SARS-CoV-2 infection.

The term "at risk of coronavirus infection", as used herein, includes reference to subjects that do not have a (measurable) coronavirus infection but which are at risk of coronavirus infection because they e.g. have been in recent (corona)virus-transmissible contact with a subject who at that moment had a coronavirus infection such as a subject from the same household, family, group of friends, work place, etc.

The term "therapeutically effective amount", as used herein, includes reference to an amount of a BAF complex modulating compound as disclosed herein that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "treating" or "treatment", as used herein, unless otherwise indicated, includes reference to reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, includes reference to the act of treating. For the avoidance of doubt, reference herein to "treatment" explicitly includes reference to both curative and prophylactic (preventative) treatment, and to the administration of a medicament for use in such treatment. Thus, preferably, the term "treatment", as used herein, includes reference to a therapeutic treatment of a coronavirus infection (such as coronavirus disease) or may also refer to a prophylactic (preventative) treatment, i.e. preventing, coronavirus infection in a subject. A viral infection preferably involves the entry in cells of the body by the virus followed by viral replication and/or release of virus particles from the infected cell.

The term "immunocompromised", as used herein, includes reference to a subject with an immune system that is weakened (such as an immune system that is deficient or suppressed) to such an extent that it has a reduced ability to fight infections such as opportunistic infections and/or other diseases. An immune system can become weakened by certain diseases or conditions, such as AIDS, cancer, diabetes, malnutrition, and certain genetic disorders. An immune system can also become weakened by being subjected to certain immunosuppressive medicaments or therapies.

The terms "bafcilin" and "baficilin" can be used interchangeably herein. Examples of terms that may be used interchangeably are bafcilin1 and baficilin1.

The term "pharmaceutically acceptable", as used herein, includes reference to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The term "carrier", as used herein, includes reference to e.g. a diluent, adjuvant, excipient, or vehicle with which a compound as disclosed herein is administered. Such pharmaceutical carriers can be liquids, such as water, saline, aqueous solutions and the like. When administered to a subject, the pharmaceutical compositions as disclosed herein are preferably sterile. An aqueous liquid such as water is a preferred vehicle when a compound as disclosed herein is administered parenterally such as intravenously. Saline solutions and aqueous dextrose solutions can also be employed as liquid vehicles, particularly for injectable solutions. The pharmaceutical compositions as disclosed herein, if desired, can also contain minor amounts of wetting agents, or pH buffering agents. When the pharmaceutical compositions as disclosed herein are formulated for oral or other forms of administration, the BAF complex modulating compound may be formulated with one or more pharmaceutically acceptable carriers such as starch, lactose, microcrystalline cellulose, silicon dioxide and/or a cyclic oligosaccharide such as cyclodextrin. Additional ingredients, in this or other embodiments of this invention may include lubricants such as magnesium stearate and/or calcium stearate.

In pharmaceutical compositions as disclosed herein, pharmaceutically acceptable carriers for use with BAF complex modulation compounds as disclosed herein may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Carriers that constitute parenteral vehicles include sodium chloride solution, Ringer's dextrose, dextrose and sodium chloride, lactated Ringer's or fixed oils. Carriers that constitute intravenous vehicles include fluid and nutrient replenishers, electrolyte replenishers (such as those based on Ringer's dextrose), and the like. A composition comprising an active agent may also be lyophilized using means well known in the art, for subsequent reconstitution and use according to the invention.

In some embodiments of a pharmaceutical composition, a BAF complex modulating compound as disclosed herein is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like.

The term 'intranasally', as used herein, may also be referred to as 'nasal administration', and includes reference to a route of administration in which a drug is provided through the nostrils into the upper respiratory tract as part of a prophylactic and/or therapeutic treatment as disclosed herein. Preferably, this form of administration provides for drug in the nasal cavity.

The term 'oral inhalation', as used herein, may also be referred to as 'mouth inhalation', and includes reference to a route of administration in which a drug is provided through the mouth to the respiratory tract, preferably lower respiratory tract such as lungs, as part of a prophylactic and/or therapeutic treatment as disclosed herein. Oral inhalation may for example be applied for drugs in their powdered form and drugs in the form of liquid droplets or aerosols.

BAF Complex Modulating Compounds

The BAF complex modulating compounds as disclosed herein, and their method of manufacture, have previously been described in relation to HIV latency reversal (WO 2020/014524 A1) and cancer combination therapies (US 2020/0255416 A1), which documents are hereby incorporated by reference especially embodiments directed to the compounds and their formulation such as the embodiments disclosed in WO 2020/014524 A1 on page 6, line 24-page 17, line 5, which relate to BAF complex modulating compounds, and page 17, line 6-page 23, line 29, which relate to formulations, dosages and routes of administration of said BAF complex modulating compounds.

The inventors have now discovered that these compounds inhibit coronavirus replication (Example 1, FIG. 1). These effects were seen in organoid-derived bronchiolar and bronchioalveolar cell cultures. Further, RNA sequencing experimentation and subsequent gene set enrichment analysis showed that genes downregulated by treatment with compounds as disclosed herein were enriched for genes that are normally upregulated during coronavirus infection, and vice versa. This suggests that the compounds disclosed herein antagonize the transcriptional program induced by coronavirus infection.

Exemplary BAF modulating compounds that can be used as a coronavirus antiviral are defined in formulas I-III and structures 1-14 such as bafcilin1, which are disclosed hereinabove in the Summary section and hereinbelow, or pharmaceutically acceptable forms thereof such as a pharmaceutically acceptable salt, polymorph, hydrate, solvate, prodrug or active metabolites thereof. In some embodiments, depending on the particular BAF complex modulation compound, a salt of the compound may be advantageous due to one or more of the salt's physical properties, such as enhanced pharmaceutical stability in differing temperatures and humidifies, or a desirable solubility in water or oil. In some instances, a salt of a compound also may be used as an aid in the isolation, purification, and/or resolution of the compound.

Preferably, the BAF modulating compounds as disclosed herein are non-toxic e.g. when administered in a therapeutically effective dose.

In another aspect, the invention provides a compound of any one of structures (11)-(14) as disclosed herein, or pharmaceutically acceptable forms thereof such as a pharmaceutically acceptable salt, polymorph, hydrate, solvate, prodrug or active metabolites thereof.

Pharmaceutical Compositions, Routes of Administration and Dosages

In the medical methods disclosed herein, the BAF complex modulating compound is preferably for administration in the form of a pharmaceutical composition.

Therefore, in aspects, the invention provides a pharmaceutical composition comprising a BAF complex modulating compound and a pharmaceutically acceptable carrier, for use as a coronavirus antiviral in a subject. In the same manner, the invention provides a method for treating or preventing a coronavirus infection in a subject, comprising the step of:—administering a therapeutically effective amount of a pharmaceutical composition comprising a BAF complex modulating compound and a pharmaceutically acceptable carrier, to a subject in need thereof.

The pharmaceutically acceptable carrier can be a solid, a liquid, or both, and may be formulated with the BAF complex modulating compound as a unit-dose composition, for example, a capsule, tablet or pill, which may comprise from 0.05% to 95% by weight of the active compounds. Other pharmacologically active substances may also be present in said composition.

The BAF complex modulating compounds disclosed herein may be administered by any suitable route, preferably in the form of a pharmaceutical composition adapted to such a route, and in a dose effective for the treatment intended. The BAF complex modulating compounds, and their compositions, for example, may be administered orally; parenterally such as intravenously; intranasally; or by oral inhalation.

Oral administration, a form of enteral administration, can be performed using a solid dose form, for example, discrete units, such as hard or soft capsules, pills, cachets, lozenges, or tablets, each containing a predetermined amount of at least one BAF complex modulating compound as disclosed herein. In another embodiment, the oral administration may be in a powder or granule form. In preferred embodiments, the BAF complex modulating compound is formulated as a capsule, pill or tablet. Such a capsule or pill may comprise excipients such as croscarmellose hydroxypropyl cellulose, magnesium stearate and/or microcrystalline cellulose.

In another embodiment, the oral dose form is sub-lingual, such as, for example, a lozenge. In such solid dosage forms, the BAF complex modulating compound as disclosed herein are ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, BAF complex modulating compounds as disclosed herein, and their pharmaceutical compositions, can be administered in a parenteral dose form. Parenteral administration includes, for example, subcutaneous injections, intravenous injections, intraperitoneal injections, intramuscular injections, intrasternal injections, and infusion. Injectable preparations (e.g., sterile injectable aqueous suspensions) may be routinely formulated according to known methods using suitable dispersing, wetting agents, and/or suspending agents. Preferably, when a BAF complex modulating compound as disclosed herein, and its pharmaceutical compositions, are administered parenterally, the administration is intravenously. An BAF complex modulating compound as disclosed herein can be formulated into a pharmaceutical composition for injection by dissolving, suspending or emulsifying the compound in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In another embodiment, BAF complex modulating compounds as disclosed herein, and their pharmaceutical compositions, can be administered in a topical dose form. Topical administration includes, for example, intranasal or (oral) inhalation administration. For intranasal administration or administration by inhalation, the BAF complex modulating compounds as disclosed herein, and their pharmaceutical compositions, can be conveniently delivered in the form of a solution or suspension from a pump spray container that is squeezed or pumped by the subject or as an aerosol spray from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer, or nebulizer, with or without the use of a suitable propellant, such as 1,1,1,2-tetrafluoroethane or 1,1,1,2,3,3,3-heptafluoropropane. In embodiments wherein the BAF complex modulating compound is for intranasal use, the powder may comprise a bioadhesive agent, for example, chitosan or cyclodextrin.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pennsylvania, 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

BAF complex modulating compounds as disclosed herein are administered at therapeutically effective dosages.

The dosage of the BAF complex modulating compound and/or pharmaceutical compositions containing said compound is based on a variety of factors, including the age, weight, sex, severity of the medical condition to be treated, and the route of administration.

In embodiments, a BAF complex modulating compound as disclosed herein can be administered in a dose that ranges from 0.1-2000 mg per dose, such as 0.1-50 mg per dose, 1-50 mg per dose, 1-100 mg per dose, 50-100 mg per dose, 100-150 mg per dose, 150-200 mg per dose, 200-250 mg per dose, 250-300 mg per dose, 300-400 mg per dose, 400-500 mg per dose, 500-600 mg per dose, 600-800 mg per dose, 800-1000 mg per dose, 1000-1400 mg per dose or 1400-2000 mg per dose.

In embodiments, dosage regimens that provide for about 0.01 mg to about 100 mg per kilogram of body weight per day may be used in the treatment or prevention of a coronavirus infection. In one embodiment, the total daily dose of a BAF complex modulating compound as disclosed herein (administered as a single daily dose or multiple daily doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg BAF complex modulating compound as disclosed herein per kg body weight). In one embodiment, dosing is from 0.01 to 10 mg/kg/day. In another embodiment, dosing is from 0.1 to 1.0 mg/kg/day. In one embodiment, a BAF complex modulating compound as disclosed herein is for administration at a dose of about 10 mg/kg, for instance 10 mg/kg/day for at least 1, 2, 3, 4, 5, 6 or 7 days (e.g. once or twice a day).

In embodiments, a BAF complex modulating compound as disclosed herein is for daily administration or is for administration multiple times per day, for instance two times a day, three times a day or four times a day. In other embodiments, a BAF complex modulating compound as disclosed herein is for administration every other day, three times a week, two times a week or once a week.

In embodiments, a BAF complex modulating compound as disclosed herein is for administration during a period of time of at least one week, at least two weeks, at least three weeks or at least one month. Preferably, a BAF complex modulating compound as disclosed herein is for administration during a period of time of at least one week or at least two weeks, such as about one week or about two weeks.

Treatment

The invention provides a BAF complex modulating compound as disclosed herein for use as a coronavirus antiviral, e.g. a SARS-CoV or MERS-CoV antiviral, preferably a SARS-CoV-2 antiviral. In other words, the invention provides a BAF complex modulating compound as disclosed herein for use in a method for treatment or prevention of a coronavirus infection in a subject in need thereof. Preferably, the coronavirus infection is a SARS-CoV infection, more preferably a SARS-CoV-2 infection.

Preferably, the subject is a mammal such as a human individual that has a coronavirus infection or is at risk of coronavirus infection. A subject, such as a human individual, can be at risk of coronavirus infection when the subject has been in coronavirus-transmissible contact with a subject that has a coronavirus infection.

Preferably, the subject, which term can be used interchangeably with the term "patient" or "individual", is a mammal, preferably a human, who is in need of treatment or prevention of a coronavirus infection. The subject can be at least 30 or at least 40 years old. More preferably, the subject is at least 50, 51, 52, 53, 54, 55, 56, 57, 58, 59, 60, 61, 62, 63, 64 or at least 65 years old and/or is an individual that is immunocompromised (also referred to as immunosuppressed). Even more preferably, a subject is at least 66, 67, 68, 69 or at least 70 or at least 80 years old.

In preferred embodiments, the subject has one or more risk factors associated with developing severe (including critical) coronavirus disease. For instance, in preferred embodiments, the subject (i) is at least 50, at least 65 or at least 70 years old, (ii) is immunocompromised and/or (iii) has at least one underlying medical condition selected from the group consisting of asthma; COPD; cystic fibrosis; pulmonary fibrosis; cardiomyopathy; pulmonary hypertension; congenital heart disease; heart failure; coronary artery disease; diabetes; obesity; cancer such as lung cancer; kidney disease; liver disease and Down syndrome. For completeness sake, in some embodiments, the subject is defined by (i) and (ii), (i) and (iii), (ii) and (iii) or (i), (ii) and (iii).

In preferred embodiments, the subject has tested positive for a coronavirus (infection), such as SARS-CoV-2 (infection), by a diagnostic test (e.g. by a nasopharyngeal swab followed by antigen- or PCR-based testing for the presence of a coronavirus (infection).

Alternatively, or in combination with said previous embodiments, the subject (i) did not previously have coronavirus disease (COVID), (ii) was not vaccinated against coronavirus disease 1-14 days, preferably 1-7 days, prior to administration of said BAF complex modulating compound and/or (iii) does not show any sign and/or symptom of coronavirus disease (COVID) when administration of said BAF complex modulating compound starts. For completeness sake, in some embodiments, the subject is defined by (i) and (ii), (i) and (iii), (ii) and (iii) or (i), (ii) and (iii); and, optionally in addition, the subject can is at least 50 or at least 65 years old, (ii) is immunocompromised and/or (iii) has at least one underlying medical condition selected from the group consisting of asthma; COPD; cystic fibrosis; pulmonary fibrosis; cardiomyopathy; pulmonary hypertension; congenital heart disease; heart failure; coronary artery disease; diabetes; obesity; cancer such as lung cancer; kidney disease; liver disease and Down syndrome.

In some embodiments, the subject is a non-hospitalized Covid-19 patient with at least one risk factor associated with developing severe (including critical) coronavirus disease.

In embodiments, a BAF complex modulating compound as disclosed herein is for parenteral administration or enteral administration. Preferably, said BAF complex modulating compound as disclosed herein is for oral, intravenous, intranasal or (oral) inhalational administration. In embodiments, said BAF complex modulating compound as disclosed herein is for oral administration daily or bidaily for 1-14 days, e.g. 1.10 or 1-7 days, preferably wherein said compound is for administration in a unit dose of 0.1-2000 mg.

In embodiments, a BAF complex modulating compound as disclosed herein can be administered alone or in combination with one or more additional therapeutic agents.

By "administered in combination" or "combination therapy" it is meant that a BAF complex modulating compound as disclosed herein and one or more additional therapeutic agents are administered concurrently to the subject being treated. When administered in combination each therapeutic agent may be administered at the same time or sequentially in any order at different points in time. Thus, each agent may be administered separately but sufficiently closely in time so as to provide the desired therapeutic effect. Thus, the medical methods as disclosed herein include use of combination agents.

More specifically, the invention provides a BAF complex modulating compound as disclosed herein for use in a method of treatment or prevention of a coronavirus infection in a subject; wherein the method comprises administration of a further therapeutic agent. Preferably, the further therapeutic agent is an immunosuppressant, e.g. dexamethasone.

For the purpose of clarity and a concise description, features may be described herein as part of the same or separate embodiments, however, it will be appreciated that the disclosure includes embodiments having combinations of all or some of the features described. For example, references to "method for treating", "treatment method", "compound for use" and "use of a compound in the manufacture of a medicament" can all be used interchangeably and embodiments disclosed in relation to any one of those aspects also applies in relation to said other aspects. In other words, they all refer to medical treatments involving a BAF complex modulating compound as disclosed herein.

The content of the documents referred to herein is incorporated by reference, especially embodiments of BAF complex modulating compounds as disclosed in WO 2020/014524 A1 and US 2020/0255416 A1.

Examples

Example 1. Inhibition of SARS-CoV2 Replication in Bronchiolar Organoid-Derived Cultures Organoid-derived 2D bronchiolar and bronchioalveolar cultures were grown as previously described (Lamers et al., EMBO J. 2020;40(5):e105912). SARS-CoV-2 isolate Bavpat-1 was propagated and titrated on Calu-3 cells as previously described (Lamers et al., Elife. 2021;10:e66815).

Twenty-four hours prior to infection, cultures were treated with (i) 1 or 10 µM Bafcilin1 (BRD-K98645985; CAS No.:1357647-78-9; see structure below), (ii) 'inactive' Bafcilin (iBafcilin; BRD-K04244835 as disclosed in Marian et al., 2018, Cell Chemical Biology 25, 1443-1455; control 1), or vehicle (DMSO; control 2) on the basal side of the transwell inserts in fresh medium (Lamers et al., The EMBO Journal, 40:e105912 (2021)). iBafcilin is about 100 times less active than Bafcilin1.

Bronchiolar and bronchioalveolar cultures were infected at a multiplicity of infection (MOI) of 0.1 with SARS-CoV-2, which means that 0.1 virus particle per cell was added. At the 2, 24, 48, and 72 hours post-infection (h p.i.), the apical side of the cultures were washed with advanced DMEM/F12 medium (Gibco). RNA was extracted from cells and RT-qPCR was performed as previously described (Lamers et al., Science. 2020; 369(6499):50-54). Ct values were compared to a titrated standard to generate TCID50 equivalents (eq.) per ml.

Experiments were performed in duplicate.

Bafcilin 1

Results

In bronchiolar organoid-derived cultures both 1 and 10 µM Bafcilin1 inhibited SARS-CoV-2 replication as compared to the DMSO control (FIG. 1A-B). Inactive Bafcilin (iBafcilin) did not inhibit SARS-CoV-2 replication at 1 µM, but did have a modest effect at 10 µM, which could be explained by the fact that iBafcilin still inhibits BAF albeit with a much lower potency than Bafcilin1. These effects were most pronounced at 72 h p.i. (FIG. 1B). In bronchioalveolar organoid-derived cultures, 10 µM Bafcilin1 inhibited SARS-CoV-2 replication (FIG. 1C-D). These results show that BAF complex modulating compounds as disclosed herein inhibit SARS-CoV-2 replication.

Example 2. BAF Complex Modulating Compounds as Disclosed Herein Antagonize Transcriptional Program Induced by Coronavirus Infection Bronchiolar organoid-derived cultures as described in Example 1 were treated for 24 h with either DMSO (control vehicle) or Bafcilin1 (1 µM or 10 µM) after which RNA was isolated using Trizol reagent (Sigma) according to manufacturer's instructions and sequenced using the 3' mRNA-Seq Library Prep Kit Protocol for Ion Torrent (QuantSeq-LEXOGEN™, Vienna, Austria), according to manufacturer's instructions. It was established that, as compared to treatment with DMSO, expression of 653 genes was affected (i.e. differentially expressed) in cells treated with 1 µM Bafcilin1 and expression of 2938 genes was affected (i.e. differentially expressed (p-value less than 0.05)) in cells treated with 10 µM Bafcilin1, of which 437 genes were found to be in common (i.e. these 437 genes were differentially expressed (in the same direction) in both the 1 µM and 10 µM Bafcilin1 group as compared to DMSO control group).

Subsequently, comprehensive gene set enrichment analysis (GSEA) using Enrichr (Enrichr (maayanlab.cloud)) of the Bafcilin1 treatment affected genes was performed, using the public COVID-19 Related Gene Sets (legacy gene set)

contained in Enricher (http://maayanlab.cloud/Enrichr/#meta!meta=Sars). GSEA of the Baficilin1 treatment (1 µM, 10 µM and common between both treatments) affected genes revealed significant enrichment of genes upregulated upon SARS-CoV-2 infection. Further, Enrichr analysis of the up and down regulated genes upon Bafcilin1 treatment of bronchiolar organoid-derived cultures as described in Example 1 at an exemplary concentration of 10 µM revealed that genes downregulated by Bafcilin1 treatment were enriched for genes upregulated upon SARS-CoV-2 or SARS-CoV-1 infection, while genes upregulated by Bafcilin1 treatment were enriched for genes downregulated upon SARS-CoV-2 or MERS-CoV infection. It is noted that the public COVID-19 Related Gene Sets (legacy gene set) also includes SARS-CoV-1 and MERS-CoV data sets.

This strongly suggests that BAF complex modulating compounds as disclosed herein, such as Bafcilin1, antagonize the transcriptional program induced by infection with coronaviruses such as SARS-CoV-2.

The invention claimed is:

1. A method for counteracting or inhibiting coronavirus replication in a subject, wherein the method comprises administering to the subject in need thereof a therapeutically effective amount of a compound of Formula (I):

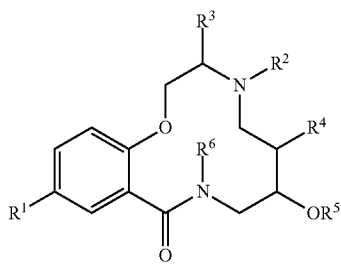

or a pharmaceutically acceptable salt or stereoisomer thereof,
wherein:
$R^1$ is $NHR^{10}$, $NHC(O)R^8$, $NHC(O)NHR^7$, or $NHC(O)OR^9$;
$R^7$ is alkyl, cycloalkyl, heterocyclyl, aryl, or heteroaryl;
$R^8$ is alkyl, cycloalkyl, heterocyclyl, aryl, or heteroaryl;
$R^9$ is alkyl, cycloalkyl, heterocyclyl, aryl, or heteroaryl;
$R^{10}$ is H, alkyl, cycloalkyl, heterocyclyl, aryl, or heteroaryl;
(i) $R^2$ is Formula (IC):

$$L^1\text{-}Z \quad (IC)$$

wherein:
$L^1$ is alkylene; and
Z is heteroarylene-aryl or arylene-heteroaryl; or
(ii) $R^2$ is Formula (ID):

$$L^2\text{-}C(O)\text{-}L^3\text{-}R^{11} \quad (ID)$$

wherein:
$L^2$ is a covalent bond or alkylene;
$L^3$ is a covalent bond or alkylene; and
$R^{11}$ is alkyl, $C_{3\text{-}10}$ cycloalkyl, or $C_{3\text{-}10}$ heterocyclyl;
$R^3$ is H or alkyl;
$R^4$ is H or alkyl;
$R^5$ is H or alkyl; and
$R^6$ is H or alkyl; and
wherein the coronavirus replication is of a coronavirus selected from the group consisting of MERS-CoV, SARS-CoV-1, and SARS-CoV-2.

2. The method according to claim 1, wherein the compound, or a pharmaceutically acceptable salt or stereoisomer thereof, specifically inhibits a BAF complex.

3. The method according to claim 2, wherein the BAF complex is an ARIDIA-containing BAF complex.

4. A method for treating a coronavirus infection in a subject, wherein the method comprises administering to the subject in need thereof a therapeutically effective amount of a compound of Formula (I):

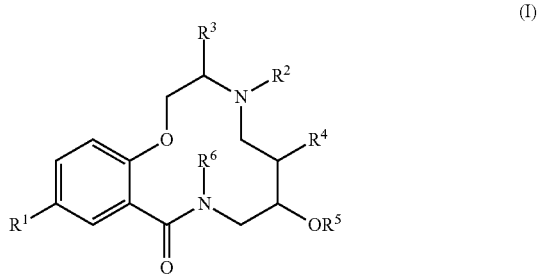

or a pharmaceutically acceptable salt or stereoisomer thereof,
wherein:
$R^1$ is $NHR^{10}$, $NHC(O)R^8$, $NHC(O)NHR^7$, or $NHC(O)OR^9$;
$R^7$ is alkyl, cycloalkyl, heterocyclyl, aryl, or heteroaryl;
$R^8$ is alkyl, cycloalkyl, heterocyclyl, aryl, or heteroaryl;
$R^9$ is alkyl, cycloalkyl, heterocyclyl, aryl, or heteroaryl;
$R^{10}$ is H, alkyl, cycloalkyl, heterocyclyl, aryl, or heteroaryl;
(i) $R^2$ is Formula (IC):

$$L^1\text{-}Z \quad (IC)$$

wherein:
$L^1$ is alkylene; and
Z is heteroarylene-aryl or arylene-heteroaryl; or
(ii) $R^2$ is Formula (ID):

$$L^2\text{-}C(O)\text{-}L^3\text{-}R^{11} \quad (ID)$$

wherein:
$L^2$ is a covalent bond or alkylene;
$L^3$ is a covalent bond or alkylene; and
$R^{11}$ is alkyl, $C_{3\text{-}10}$ cycloalkyl, or $C_{3\text{-}10}$ heterocyclyl;
$R^3$ is H or alkyl;
$R^4$ is H or alkyl;
$R^5$ is H or alkyl; and
$R^6$ is H or alkyl; and
wherein the coronavirus infection is selected from the group consisting of a MERS-CoV infection, a SARS-CoV-1 infection, and a SARS-CoV-2 infection.

5. The method according to claim 4, wherein:
(a) the subject is at risk of contracting a coronavirus infection; or
(b) the subject has a coronavirus infection.

6. The method according to claim 4, wherein:
(a) the subject is at least 65 years old; or
(b) the subject is immunocompromised; or
(c) the subject has at least one underlying medical condition selected from the group consisting of asthma, cancer, cardiomyopathy, chronic obstructive pulmonary disease (COPD), congenital heart disease, coronary artery disease, cystic fibrosis, diabetes, Down syndrome, heart failure, kidney disease, liver disease, obesity, pulmonary fibrosis, and pulmonary hypertension; or (d) the subject is at least 65 years old; and
the subject is immunocompromised; or
(e) the subject is at least 65 years old; and
the subject has at least one underlying medical condition selected from the group consisting of asthma, cancer, cardiomyopathy, chronic obstructive pulmonary disease (COPD), congenital heart disease, coronary artery disease, cystic fibrosis, diabetes, Down syndrome, heart failure, kidney disease, liver disease, obesity, pulmonary fibrosis, and pulmonary hypertension; or
(f) the subject is immunocompromised; and
the subject has at least one underlying medical condition selected from the group consisting of asthma, cancer, cardiomyopathy, chronic obstructive pulmonary disease (COPD), congenital heart disease, coronary artery disease, cystic fibrosis, diabetes, Down syndrome, heart failure, kidney disease, liver disease, obesity, pulmonary fibrosis, and pulmonary hypertension; or
(g) the subject is at least 65 years old;
the subject is immunocompromised; and
the subject has at least one underlying medical condition selected from the group consisting of asthma, cancer, cardiomyopathy, chronic obstructive pulmonary disease (COPD), congenital heart disease, coronary artery disease, cystic fibrosis, diabetes, Down syndrome, heart failure, kidney disease, liver disease, obesity, pulmonary fibrosis, and pulmonary hypertension.

7. The method according to claim 4, wherein the coronavirus infection is a SARS-CoV-2 infection.

8. The method according to claim 4, wherein the compound, or stereoisomer thereof, is of Formula (IA):

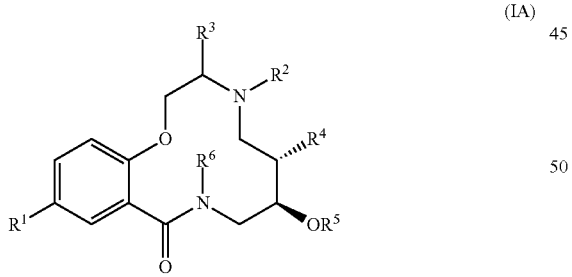

or a pharmaceutically acceptable salt thereof.

9. The method according to claim 4, wherein $R^1$ is $NHC(O)NHR^7$.

10. The method according to claim 4, wherein $R^2$ is Formula (IC):

$$L^1\text{-}Z \quad \text{(IC)}.$$

11. The method according to claim 4, wherein the compound, or stereoisomer thereof, is of Formula (II):

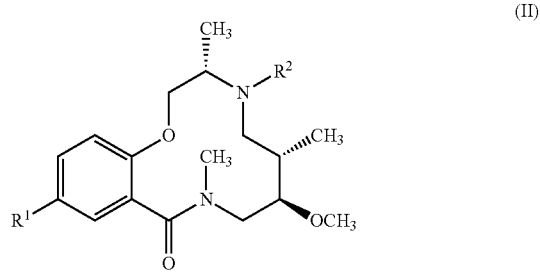

or a pharmaceutically acceptable salt thereof, $R^1$ is $NHR^{10}$, $NHC(O)R^8$, $NHC(O)NHR^7$, or $NHC(O)OR^9$;

$R^7$ is $CH_3$, $CH_2CH_3$, $CH_2CH_2CH_3$, $CH(CH_3)_2$, $CH_2CH_2CH_2CH_3$, $CH(CH_3)CH_2CH_3$, $C(CH_3)_3$, $CH_2CH_2CH_2CH_2CH_3$, $CH_2CH_2CH_2CH_2CH_2CH_3$, cycloalkyl, heterocyclyl, aryl, or heteroaryl;

$R^8$ is $CH_3$, $CH_2CH_3$, $CH_2CH_2CH_3$, $CH(CH_3)_2$, $CH_2CH_2CH_2CH_3$, $CH(CH_3)CH_2CH_3$, $C(CH_3)_3$, $CH_2CH_2CH_2CH_2CH_3$, $CH_2CH_2CH_2CH_2CH_2CH_3$, cycloalkyl, heterocyclyl, aryl, or heteroaryl;

$R^9$ is $CH_3$, $CH_2CH_3$, $CH_2CH_2CH_3$, $CH(CH_3)_2$, $CH_2CH_2CH_2CH_3$, $CH(CH_3)CH_2CH_3$, $C(CH_3)_3$, $CH_2CH_2CH_2CH_2CH_3$, $CH_2CH_2CH_2CH_2CH_2CH_3$, cycloalkyl, heterocyclyl, aryl, or heteroaryl;

$R^{10}$ is H, alkyl, cycloalkyl, heterocyclyl, aryl, or heteroaryl; and $R^2$ is:

12. The method according to claim 4, wherein the compound, or stereoisomer thereof, is:

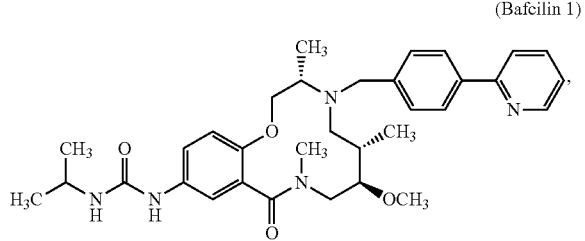 [SMILES: CO[C@H]1CN(C)C(=O)c2cc(NC(=O)NC(C)C)ccc2OC[C@H](C)N(Cc2ccc(-c3ccccn3)cc2)C[C@@H]1C]

(Bafcilin 1)

or a pharmaceutically acceptable salt thereof.

13. The method according to claim 4, wherein the compound, or a pharmaceutically acceptable salt or stereoisomer thereof, specifically inhibits a BAF complex.

14. The method according to claim 13, wherein the BAF complex is an ARIDIA-containing BAF complex.

15. The method according to claim 4, wherein the method further comprises intranasally, intravenously, or orally administering to the subject in need thereof a therapeutically effective amount of the compound of Formula (I), or a pharmaceutically acceptable salt or stereoisomer thereof.

16. The method according to claim 15, wherein the oral administration is performed via inhalation.

17. The method according to claim 4, wherein the method further comprises orally administering to the subject in need thereof a therapeutically effective amount of the compound of Formula (I), or a pharmaceutically acceptable salt or stereoisomer thereof, daily or bidaily for a period in the range of 1 day to 14 days.

* * * * *